United States Patent
Dupuis

[11] Patent Number: 5,620,684
[45] Date of Patent: Apr. 15, 1997

[54] COSMETIC COMPOSITIONS FOR MAINTAINING HAIRSTYLE POSSESSING IMPROVED FIXING POWER

[75] Inventor: Christine Dupuis, Paris, France

[73] Assignee: L'Oreal, Paris, France

[21] Appl. No.: 636,270

[22] Filed: Apr. 29, 1996

Related U.S. Application Data

[63] Continuation of Ser. No. 278,548, Jul. 21, 1994, abandoned.

[30] Foreign Application Priority Data

Jul. 23, 1993 [FR] France ................... 93 09096

[51] Int. Cl.$^6$ .................................. A61K 7/11
[52] U.S. Cl. .................. 424/70.12; 424/70.19; 424/70.22; 424/70.24
[58] Field of Search ............. 424/70.12, 70.19, 424/70.22, 70.24

[56] References Cited

U.S. PATENT DOCUMENTS

| | | | |
|---|---|---|---|
| 2,961,431 | 11/1960 | Kutner | 260/79.3 |
| 4,128,631 | 12/1978 | Lundmark et al. | 424/70 |
| 4,138,477 | 2/1979 | Gaffar | 424/52 |
| 5,472,686 | 12/1995 | Tsubaki et al. | 424/59 |

FOREIGN PATENT DOCUMENTS

| | | |
|---|---|---|
| 1010365 | 5/1977 | Canada. |
| 0492657A1 | 7/1992 | European Pat. Off.. |
| 0535367A2 | 4/1993 | European Pat. Off.. |
| 2238474 | 3/1975 | France. |
| 2034724 | 6/1980 | United Kingdom. |

*Primary Examiner*—Jyothsna Venkat
*Attorney, Agent, or Firm*—Finnegan, Henderson, Farabow, Garrett & Dunner, L.L.P.

[57] ABSTRACT

The invention relates to improving the fixing power of cosmetic compositions intended for maintaining hairstyle and containing an anionic polymer.

It relates to the use of a polysiloxane/polyoxyalkyene linear block copolymer as an agent for enhancing the fixing power of a composition for maintaining hairstyle containing an anionic polymer.

10 Claims, No Drawings

COSMETIC COMPOSITIONS FOR MAINTAINING HAIRSTYLE POSSESSING IMPROVED FIXING POWER

This application is a continuation of application Ser. No. 08/278,548, filed Jul. 21, 1994, now abandoned.

The present invention relates to cosmetic compositions for maintaining hairstyle which contain linear block copolymers and an anionic polymer and which possess improved fixing power. The present invention also relates to a method for enhancing the fixing power of a cosmetic composition for maintaining hairstyle.

In the context of the present application, cosmetic compositions for maintaining hairstyle are compositions directed towards temporarily fixing the shape of the hairstyle, such as, for example, fixing hair sprays, setting compositions, styling foams, gels and sprays. The fixing power of the compositions denotes the capacity of the compositions to provide cohesive characteristics to the hair, such that the initial shaping of the hairstyle is temporarily preserved.

The use of silicone derivatives in combination with polymer resins is widely known in the preparation of cosmetic compositions for maintaining hairstyle. It has been established that the silicone derivatives markedly improve the disentangling, softness and sheen properties of hair treated with these compositions. On the other hand, the silicone derivatives tend to deteriorate the fixing power of these compositions, which fixing power is provided by the polymer resins.

Application EP 492,657 A1 describes the use of polysiloxane/polyoxyalkylene linear block copolymers in cosmetic compositions which are useful for skin and hair care. According to EPA 492,657 A1, the use of polysiloxane/polyoxyalkylene linear block copolymers, alone or in combination with an agent for the treatment of the skin or hair, provides the properties of improved sheen, durability and/or softness to the formulation to be obtained. These linear block copolymers are described in a general manner as providing, relative to the silicone compounds of the prior art used in these compositions, properties of the same nature but of a substantially higher degree.

A person skilled in the art would thus expect the copolymers described in EPA 492,657 A1 to further aggravate the deterioration of the fixing power, even though, in other respects, one would expect an improvement of the disentangling, sheen, and softness properties. This point is not refuted upon a reading of the examples in EPA 492,657 A1, in particular of Example 19. Because there is no anionic polymer in Example 19, it is believed the reproduction of Example 19 would yield a composition having very low fixing power, which would be incompatible with a marketing of this composition for the maintenance of hairstyle.

It is further described in the above-discussed European application that the polysiloxane/polyoxyalkylene linear block copolymers may be used in combination with additives including high molecular weight compounds, for instance, in particular, the following three polymers: maleic anhydride/methyl vinyl ether copolymer monoesterified with a lower alcohol, vinyl acetate/crotonic acid copolymer and acrylic acid/acrylic ester/N-alkylacrylamide copolymer. These three additive compounds are in no way singled out as anionic polymers providing special properties.

In addition, there is no mention within the above-discussed European application of the specific value which might be possessed by these linear block copolymers for producing compositions for maintaining hairstyle which possess improved fixing power.

The present invention has made it possible to overcome the problems left by the prior art.

The object of the present invention is the use of a polysiloxane/polyoxyalkylene linear block copolymer as an agent for enhancing the fixing power of a composition for maintaining hairstyle, which composition contains an anionic polymer.

A method of the present invention for enhancing the fixing power of a composition for maintaining hairstyle comprises the step of combining in a composition for maintaining hairstyle a polysiloxane/polyoxyalkylene linear block copolymer with an anionic polymer for the purpose of enhancing the fixing power of said anionic polymer. The compositions of the present invention impart good disentangling, sheen and softness properties to the hair, while providing an improved fixing power.

The invention also relates to a new cosmetic composition for maintaining hairstyle which comprises a polysiloxane/polyoxyalkylene linear block copolymer and an anionic polymer, in a cosmetically acceptable carrier, excluding the following anionic polymers: maleic anhydride/methyl vinyl ether copolymer monoesterified with a lower alcohol, vinyl acetate/crotonic acid copolymer and acrylic acid/acrylic ester/N-alkylacrylamide copolymer.

According to a preferred embodiment of the invention, the anionic polymer contains a sulphonic group and is selected from polystyrenesulphonic acid salts, alkali metal and alkaline-earth metal salts of sulphonic acids derived form lignin, polyacrylamide-sulphonic acid salts, polymers containing salified alkylnaphthalenesulphonic units, polymers containing a vinylsulphonic unit and copolymers resulting from the polymerization of an unsaturated sulphonic acid and an N-monoalkylacrylamide.

Representative polystyrenesulphonic acid salts which may be used in the present invention are the sodium salts having a molecular weight of approximately 500,000 and of approximately 100,000 sold, respectively, under the names FLEXAN 500 and FLEXAN 130 by National Starch. These compounds are described in Patents FR 2,198,729 and CA 101 365, the disclosures of which are specifically incorporated by reference herein.

Representative alkali metal and alkaline-earth metal salts of sulphonic acids derived from lignin which may be used in the present invention are calcium or sodium ligonsulphonates such as the product sold under the name MARASPERSE C-21 by American Can Co. and the $C_{10}$–$C_{14}$ compounds sold by Avèbene.

Representative polyacrylamide-sulphonic acid salts which may be used in the present invention are those referred to in U.S. Pat. No. 4,128,631, the disclosure of which is specifically incorporated by reference herein, and more particularly, polyacrylamidoethyl-propanesulphonic acid, sold under the name COSMEDIA POLYMER HSP 1180 by Henkel.

A representative polymer containing salified alkylnaphthalenesulphonic acid units which may be used in the present invention is the sodium salt sold under the name DARVAN NO. 1 by Van der Bilt.

Representative polymers containing at least one vinylsulphonic unit in their chain which may be used in the present invention are polyvinylsulphonates having a molecular weight ranging from 1000 to 100,000, and in particular their sodium, potassium, calcium and ammonium salts and amine salts such as alkylamine and alkanolamine salts, as well as copolymers containing at least some vinylsulphonic groups with one or more cosmetically acceptable comonomers such as unsaturated acids chosen from acrylic and methacrylic acids and their esters, amides such as acrylamide or methacrylamide, substituted or otherwise, vinyl esters, vinyl ethers and vinylpyrrolidone. These polymers are described more particularly in French Patent 2,238,474 and U.S. Pat. Nos. 2,961,431 and 4,138,477, the disclosures of which are specifically incorporated by reference herein.

Representative copolymers resulting from the polymerization of an unsaturated sulphonic acid and an N-monoalkylacrylamide which may be used in the present invention are the polymers originating from the polymerization of a least one unsaturated sulphonic acid in a proportion of 30 to 90% by weight and having the following general formula:

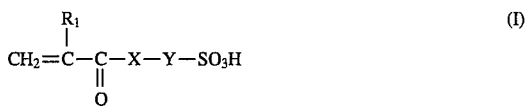

in which:

$R_1$ represents a hydrogen atom or a $CH_3$ radical;

X represents O or —NH—; and

Y represents a linear or branched alkylene chain having from 1 to 6 carbon atoms;

and at least one N-monoalkylacrylamide or N-methacrylamide in a proportion of 10 to 70% by weight and having the following general formula:

in which:

$R_2$ represents a hydrogen atom or a —$CH_3$ radical;

$R_3$ represents a linear or branched alkyl radical having from 3 to 10 carbon atoms;

the sulphonic acid functions of said polymer being neutralized in a proportion of 40 to 70% with triethanolamine.

The unsaturated sulphonic acids of 2-acrylamido-2-methylpropanesulphonic acid, 2-sulphoethyl methacrylate, N-acryloyltaurine and N-methacryloyltaurine, of formula (I), are preferred.

The N-monoalkylacrylamides or N-methacrylamides of N-tert-butylacrylamide, N-tert-hexylacrylamide and N-tert-octylacrylamide, of formula (II), are preferred.

Still more preferred is the copolymerization product of an amidosulphonic acid (X=—NH— in formula (I)) in which the alkylene chain has from 2 to 4 carbon atoms, and particularly 2-acrylamido-2-methyl-propanesulphonic acid, in a proportion of 40 to 70% by weight, and an N-monoalkylacrylamide, and particularly N-tert-butylacrylamide.

These copolymers may also take the form of ter- or tetrapolymers.

According to this embodiment, the comonomers capable of constituting the other repeat units of the copolymer may be chosen from:

(1) alkyl acrylates or methacrylates in a proportion of 3 to 40% by weight and having the following general formula:

in which:

$R_4$ represents a hydrogen atom or a —$CH_3$ radical; and $R_5$ represents a linear or branched alkyl radical having from 1 to 4 carbon atoms.

The alkyl acrylates and methacrylates of methyl acrylate, ethyl acrylate and butyl methacrylate, of formula (III), are preferred. It is further preferred to use methyl acrylate or ethyl acrylate in a proportion of 3 to 25% by weight.

(2) acrylamides and methacrylamides in a proportion of 3 to 40% by weight and having the following general formula:

in which:

$R_6$ represents a hydrogen atom or a —$CH_3$ radical; and $R_7$ and $R_8$, which may be identical or different, represent a hydrogen atom or an alkyl radical having from 1 to 4 carbon atoms, or $R_7$ represents a hydrogen atom and $R_8$ represents the radical of formula:

The acrylamides and methacrylamides of (dimethyl-3-oxobutyl)acrylamide, N,N-dimethylacrylamide and N,N-diethylacrylamide, of formula (IV), are preferred. It is further preferable to use (dimethyl-3-oxobutyl)acrylamide in a proportion of 3 to 25%.

Even more preferred copolymers are those containing repeat units derived from the copolymerization of the following compounds:

2-acrylamido-2-methylpropanesulphonic acid (62%)/N-tert-butylacrylamide (38%);

2-acrylamido-2-methylpropanesulphonic acid (40%)/N-tert-butylacrylamide (20%)/ethyl acrylate (15%)/(dimethyl-3-oxobutyl) acrylamide (25%);

2-acrylamido-2-methylpropanesulphonic acid (60%)/N-tert-butylacrylamide (20%)/(dimethyl-3-oxobutyl)acrylamide (20%);

2-acrylamido-2-methylpropanesulphonic acid (60%)/N-tert-butylacrylamide (25%)/ethyl acrylate (15%); and 2-acrylamido-2-methylpropanesulphonic acid (60%)/N-tert-butylacrylamide (25%)/methyl acrylate (15%).

According to another preferred embodiment of the invention, the anionic polymer is a polymer containing a carboxylic acid function as described in FR 2,439,798 and GB 2 034 724 A, the disclosures of which are specifically incorporated by reference herein, and having the following general formula:

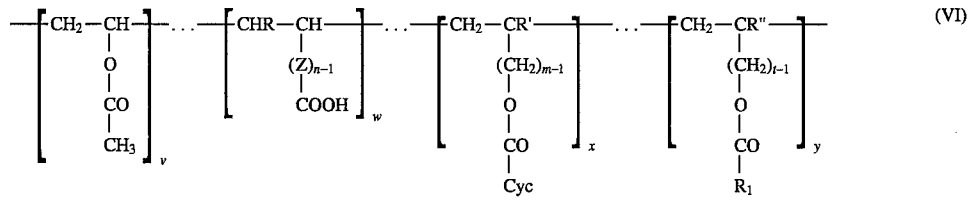

in which:

R, R' and R", which may be identical or different, represent a hydrogen atom or a methyl radical;

m, n and t are equal to 1 or 2;

$R_1$ represents a saturated or unsaturated, linear or branched alkyl radical having from 2 to 21 carbon atoms;

Z represents a divalent radical selected from: —$CH_2$—, —$CH_2$—O—$CH_2$— and —$CH_2$—O—$(CH_2)_2$—;

Cyc represents a radical selected from:

(i) a radical of the formula:

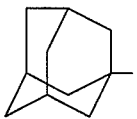

(VII)

(ii) a radical of the formula:

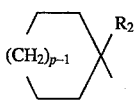

(VIII)

in which:

$R_2$ represents a hydrogen atom or a methyl radical; and p is equal to 1 or 2;

(iii) a radical of the formula:

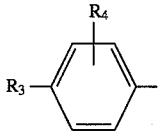

(IX)

in which:

$R_3$ represents a hydrogen atom or a methyl, ethyl, tert-butyl, ethoxy, butoxy or dodecyloxy radical;

$R_4$ represents a hydrogen atom, an alkyl radical having 1 to 4 carbon atoms or an alkoxy radical having 1 to 4 carbon atoms; and (iv) a radical of the formula:

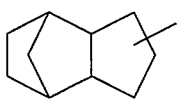

(X)

in which:

v represents from 10 to 91% and preferably from 36 to 84% by weight;

w represents from 3 to 20% and preferably from 6 to 12% by weight;

x represents from 4 to 60% and preferably from 6 to 40% by weight;

y represents form 0 to 40% and preferably from 4 to 30% by weight; and the sum of v+w+x+y is equal to 100%.

Among these compounds, it is more preferred to use a vinyl acetate/vinyl tert-butylbenzoate/crotonic acid terpolymer.

According to another preferred embodiment, the anionic polymer is a vinylpyrrolidone/(meth) acrylic acid copolymer optionally comprising other comonomers such as alkyl acrylates or methacrylates.

Representative copolymers which may be used are:

vinylpyrrolidone/acrylic acid, for instance the compounds sold under the names ACRYLIDONE ACP 1033, 1001, 1042 BY I.S.P.;

vinylpyrrolidone/methacrylic acid/t-butyl acrylate sold under the names LUVIFLEX VBM 35 and LUVIFLEX VBM 70 by BASF; and vinylpyrrolidone/acrylic acid/lauryl methacrylate sold under the name ACP-1135 by I.S.P.

According to another preferred embodiment of the invention, the anionic polymer is a (meth)acrylic acid/alkyl (meth)acrylate copolymer.

According to another preferred embodiment of the invention, the anionic polymer is an acrylic acid/N,N-dimethylacrylamide/ethyl methacrylate/N-tert-butylacrylamide copolymer.

The anionic polymers used in the present invention can, in the final compositions, be present in a solubilized state or alternatively in a dispersed state, for example in the form of a latex and/or a pseudolatex. The expression "pseudolatex" is intended to denote a stable, aqueous suspension containing fine, generally spherical particles of the anionic polymers, these particles having been obtained by dispersing, in an appropriate aqueous phase, the anionic polymer in the already synthesized state. The expression "psuedolatex" must not therefore be confused with the expressions latex and synthetic latex, which is undoubtedly also an aqueous suspension containing particles of a particle or polycondensate but in which the particles have been conventionally obtained by emulsion polymerization or polycondensation of one or more monomers in an appropriate aqueous phase.

The polysiloxane/polyoxyalkylene linear block copolymers used in the present invention preferably have the following general formula:

$$([Y(R_2SiO)_aR'_2SiYO] [(C_nH_{2n}O)_b])_c \qquad (XI)$$

in which:

R and R', which may be identical or different, represent a monovalent hydrocarbon radical not containing an aliphatic unsaturation;

n is an integer ranging from 2 to 4;

a is an integer greater than or equal to 5;

b is an integer greater than or equal to 4;

c is an integer greater than or equal to 4; and

Y represents a divalent organic group which is linked to the adjacent silicon atom via a carbon-silicon bond and to a polyoxyalkylene block via an oxygen atom.

The average molecular weight of each siloxane block ranges from approximately 400 to approximately 10,000, while, the average molecular weight of each polyoxyalkylene block ranges from approximately 300 to approximately 10,000. The siloxane blocks represent from approximately 10% to approximately 90% by weight of the block copolymer. The average molecular weight of the block copolymer is at least 3,000.

R and R' are, more preferably, chosen from the group comprising alkyl radicals such as, for example, methyl, ethyl, propyl, butyl, pentyl, hexyl, octyl, decyl and dodecyl radicals, aryl radicals such as, for example, phenyl and naphthyl, aralkyl radicals such as, for example, benzyl and phenylethyl, and tolyl, xylyl and cyclohexyl radicals.

Y is preferably —R"—, —R"—CO—, —R"—NHCO—, —R"—NH—CO—NH—R'"—NHCO— or —R"—OCONH—R'"—NHCO—, where R" is a divalent alkylene group such as, for example, ethylene, propylene or butylene and R'" is a divalent alkylene group or a divalent arylene group such as —$C_6H_4$—, —$C_6H_4$—$C_6H_4$—, —$C_6H_4$—$CH_2$—$C_6H_4$— or —$C_6H_4$—$C(CH_3)_2$—$C_6H_4$—.

Still more preferably, Y represents a divalent alkylene radical, and more particularly a —$CH_2$—$CH_2$—$CH_2$— radical.

The preparation of the block copolymers employed in the present invention is described in European Application EP 0,492,657 A1, the disclosure of which is specifically incorporated by reference herein.

Preferred polysiloxane/polyoxyalkylene linear block copolymers according to the invention are chosen from those of formula:

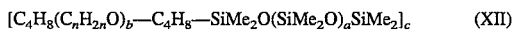

$$[C_4H_8(C_nH_{2n}O)_b\text{—}C_4H_8\text{—}SiMe_2O(SiMe_2O)_aSiMe_2]_c \qquad (XII)$$

in which:

Me represents methyl;

n is an integer from 2 to 4;

a and b are integers greater than or equal to 4; and c is a number greater than or equal to 4.

According to a preferred embodiment of the invention, the block copolymer is chosen from the following copolymers:

(1) $[[(CH_3)_2SiO]_{41}(CH_3)_2SiCH_2CH(CH_3)CH_2\text{—}O(C_2H_4O)_{18}\text{—}(C_3H_6O)_{33}CH_2CH(CH_3)CH_2]_{16.1}$;

(2) $[[(CH_3)_2SiO]_{31}(CH_3)_2SiCH_2CH(CH_3)CH_2\text{—}O(C_2H_4O)_{20}\text{—}(C_3H_6O)_{29}CH_2CH(CH_3)CH_2]_{13.3}$;

(3) $[[(CH_3)_2SiO]_9(CH_3)_2SiCH_2CH(CH_3)CH_2\text{—}O(C_2H_4O)_{20}\text{—}(C_3H_6O)_{29}CH_2CH(CH_3)CH_2]_{26.3}$;

(4) $[[(CH_3)_2SiO]_{16}(CH_3)_2SiCH_2CH(CH_3)CH_2\text{—}O(C_2H_4O)_{18}\text{—}(C_3H_6O)_{20}CH_2CH(CH_3)CH_2]_{21.5}$; and (5) $[[(CH_3)_2SiO]_9(CH_3)_2SiCH_2CH(CH_3)CH_2\text{—}O(C_2H_4O)_5\text{—}CH_2CH(CH_3)CH_2]_{4.8}$.

The anionic polymer is preferably employed in an amount ranging from 0.1 to 25% by weight of total weight of the composition. Still more preferably, this amount ranges from 0.5 to 20%.

The linear block copolymer is preferably employed in an amount ranging from 0.05 to 20% by weight of the total weight of the composition. Still more preferably, this amount ranges from 0.1 to 10%.

The compositions according to the invention can take the form of a gel, an emulsion (milk or cream), a more or less thickened aqueous, alcoholic or aqueous-alcoholic lotion, a dispersion or a foam.

The compositions of the invention are, more particularly, setting lotions, blow-drying lotions, fixing compositions (fixing hair sprays), and styling compositions.

The lotions may be packaged in various forms, in particular in vaporizers, in pump bottles or in aerosol containers so as to provide for application of the composition either in vaporized form or in the form of a foam. Such packaging forms are indicated, for example, when it is desired to obtain a spray, a fixing hair spray or a foam for fixing the hair.

The cosmetically acceptable medium (carrier) consists, for example, of water, an organic solvent such as, for example, an alcohol and mixtures thereof.

The compositions according to the invention can, in addition, contain the additives customarily used in cosmetics.

When the composition according to the invention is packaged in aerosol form for the purpose of obtaining a fixing hair spray or an aerosol foam, the composition comprises at least one propellent agent which can be chosen from volatile hydrocarbons such as n-butane, propane, isobutane, pentane and mixtures thereof, where appropriate with at least one chlorinated and/or fluorinated hydrocarbon. It is also possible to use carbon dioxide, nitrous oxide, dimethyl ether, nitrogen or compressed air as a propellent agent.

The invention will now be illustrated more completely by means of the examples which follow, which are not to be considered as limiting the invention.

EXAMPLE 1

An aerosol fixing hair spray was prepared by mixing the following ingredients:

10 g (active substance) of vinyl acetate (65%)/crotonic acid (10%)/vinyl tert-butylbenzoate (25%) copolymer;

the requisite amount of 2-amino-2-methyl-1-propanol for neutralizing 100% of the acid functions of the copolymer;

3 g of block copolymer of formula

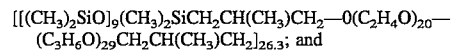

$$[[(CH_3)_2SiO]_9(CH_3)_2SiCH_2CH(CH_3)CH_2\text{—}O(C_2H_4O)_{20}\text{—}(C_3H_6O)_{29}CH_2CH(CH_3)CH_2]_{26.3}; \text{ and}$$

ethanol in a quantity sufficient to obtain 100 g of composition.

This composition was packaged in an aerosol can according to the following pressurization scheme:

above composition: 40% dimethyl ether: 40% pentane: 20%

EXAMPLE 2

An aerosol spray was prepared by mixing the following ingredients:

8 g (active substance) of vinyl acetate (65%)/crotonic acid (10%)/vinyl tert-butylbenzoate (25%) copolymer;

the requisite amount of 2-amino-2-methyl-1-propanol for neutralizing 100% of the acid functions of the copolymer;

2 g of block copolymer of formula

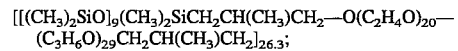

$$[[(CH_3)_2SiO]_9(CH_3)_2SiCH_2CH(CH_3)CH_2\text{—}O(C_2H_4O)_{20}\text{—}(C_3H_6O)_{29}CH_2CH(CH_3)CH_2]_{26.3};$$

10 g of ethanol; and water in a quantity sufficient to obtain 100 g of composition.

This composition was packaged according to the following pressurization scheme:

above composition: 70% dimethyl ether: 30%

EXAMPLE 3

A pump-bottle spray was prepared by mixing the following ingredients:

8 g (active substance) of vinyl acetate (65%)/crotonic acid (10%)/vinyl tert-butylbenzoate (25%) copolymer;

the requisite amount of 2-amino-2-methyl-1-propanol for neutralizing 100% of the acid functions of the copolymer;

1.5 g of block copolymer of formula

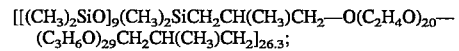

$$[[(CH_3)_2SiO]_9(CH_3)_2SiCH_2CH(CH_3)CH_2\text{—}O(C_2H_4O)_{20}\text{—}(C_3H_6O)_{29}CH_2CH(CH_3)CH_2]_{26.3};$$

15 g of water; and ethanol in a quantity sufficient to obtain 100 g of the pump bottle spray.

EXAMPLE 4

A shaping lotion was prepared by mixing the following ingredients:

0.5 g (active substance) of polyacrylamidoethylpropanesulphonic acid (sold under the name COSMEDIA POLYMER HSP 1180 by Henkel);

1 g of block copolymer of formula

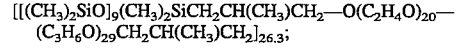

$$[[(CH_3)_2SiO]_9(CH_3)_2SiCH_2CH(CH_3)CH_2\text{—}O(C_2H_4O)_{20}\text{—}(C_3H_6O)_{29}CH_2CH(CH_3)CH_2]_{26.3};$$

8.3 g of ethanol;
perfumes and preservatives in a quantity sufficient; and
water in a quantity sufficient to obtain 100 g of the shaping lotion.

EXAMPLE 5

An aerosol fixing hair spray was prepared by mixing the following ingredients:
8 g (active substance) of vinylpyrrolidone/methacrylic acid/t-butyl acrylate terpolymer sold under the name LUVIFLEX VBM 35 by BASF;
the requisite amount of 2-amino-2-methyl-1-propanol for a 100% neutralization of the LUVIFLEX VBM 35;
2 g of block copolymer of formula $$[[(CH_3)_2SiO]_9(CH_3)_2SiCH_2CH(CH_3)CH_2\text{—}O(C_2H_4O)_{20}\text{—}(C_3H_6O)_{29}CH_2CH(CH_3)CH_2]_{26.3}; \text{ and}$$

absolute ethanol in a quantity sufficient to obtain 100 g of composition.
This composition was packaged according to the following pressurization scheme:
above composition: 37 g %
dimethyl ether: 43 g %
N-pentane: 20 g %

EXAMPLE 6

An aerosol foam was prepared by mixing the following ingredients:
1.8 g (active substance) of 2-acrylamido-2-methylpropane-sulphonic acid (62%)/N-tert-butylacrylamide (38%) copolymer;
the requisite amount of triethanolamine for a 100% neutralization of the sulphonic copolymer;
2 g of block copolymer of formula $$[[(CH_3)_2SiO]_9(CH_3)_2SiCH_2CH(CH_3)CH_2\text{—}O(C_2H_4O)_{20}\text{—}(C_3H_6O)_{29}CH_2CH(CH_3)CH_2]_{26.3};$$

20 g of absolute ethanol; and
water in a quantity sufficient to obtain 100 g of composition.
This composition was packaged according to the following pressurization scheme:
above composition: 90 g %
butane/propane/isobutane mixture sold under the name AEROGAZ 3.2N by ELF AQUITAINE: 10 g %

EXAMPLE 7

A gel was prepared by mixing the following ingredients:
2 g (active substance) of methacrylic acid (50%)/methyl methacrylate (50%) copolymer;
the requisite amount of 2-amino-2-methyl-1-propanol for a 100% neutralization of the anionic copolymer;
1 g of block copolymer of formula $$[[(CH_3)_2SiO]_9(CH_3)_2SiCH_2CH(CH_3)CH_2\text{—}O(C_2H_4O)_{20}\text{—}(C_3H_6O)_{29}CH_2CH(CH_3)CH_2]_{26.3};$$

2 g (active substance) of acrylic thickener sold under the name CARBOPOL 940 by the company GOODRICH;
40 g of absolute ethanol;
the requisite amount of 2-amino-2-methyl-1-propanol for neutralizing 100% of the acid functions of the copolymer to pH 7.6; and
water in a quantity sufficient to obtain 100 g of the gel.

EXAMPLE 8

A spray was prepared by mixing the following ingredients:
8 g (active substance) of methacrylic acid (50%)/methyl methacrylate (50%) copolymer;
the requisite amount of 2-amino-2-methyl-1-propanol for neutralizing 100% of the anionic copolymer;
2 g of block copolymer of formula $$[[(CH_3)_2SiO]_9(CH_3)_2SiCH_2CH(CH_3)CH_2\text{—}O(C_2H_4O)_{20}\text{—}(C_3H_6O)_{29}CH_2CH(CH_3)CH_2]_{26.3}; \text{ and}$$

absolute ethanol in a quantity sufficient to obtain 100 g of the spray.
The active material was packaged in a pump bottle.

EXAMPLE 9

Synthesis

One hundred (100) g of dimethacrylpolyether $(CH_2=C(CH_3)CH_2O(C_2H_4O)_{18}(C_3H_6O)_{33}CH_2C(CH_3)=CH_2)$, 350 g of toluene, and 20 ppm of platinum as chloroplatinate were put in a 500 ml-three neck flask having a mechanical agitator, a condenser, a thermometer and a port for feeding nitrogen. One hundred nine (109) g of dihydropolydimethyl polysiloxane $(HMe_2SiO(MeSiO)_{40}SiMe_2H)$ was gradually added to the mixture at such a speed that the temperature is retained at 80°–100° C.

The end of this reaction was judged when an $AgNO_3$ test on SiH became minus.

Then the reacted mixture was neutralized by $NaHCO_3$ and filtered, and the solvent was removed at 50° C./1 mmHg by a rotary evaporator. Two hundred and three (203) g of the block copolymer having the following repeating unit and a molecular weight of 95,000 was prepared.

$$[(Me_2SiO)_{41}Me_2SiCH_2CH(CH_3)CH_2\text{—}O(C_2H_4O)_{18}\text{—}(C_3H_6O)_{33}CH_2CH(CH_3)CH_2]_{16.1}.$$

What is claimed is:
1. A method for enhancing the fixing power of a composition for maintaining hairstyle comprising the step of combining in a composition for maintaining hairstyle a polysiloxane/polyoxyalkylene linear block copolymer with an anionic polymer for the purpose of enhancing the fixing power of said anionic polymer, where said polysiloxane/polyoxyalkylene linear block copolymer corresponds to the formula:

$$[C_4H_8(C_nH_{2n}O)_b\text{—}C_4H_8\text{—}SiMe_2O(SiMe_2O)_aSiMe_2]_c$$

in which:
Me represents methyl;
n is an integer from 2 to 4;
a and b are integers greater than or equal to 4; and
c is a number greater than or equal to 4; wherein the average molecular weight of each siloxane block ranges from approximately 400 to approximately 10,000; wherein the average molecular weight of each polyoxyalkylene block ranges from approximately 300 to approximately 10,000; wherein the siloxane blocks represent from approximately 10% to approximately 90% by weight of the block copolymer; and further wherein the average molecular weight of the block copolymer ranges from at least 3,000 to 95,000;

and further wherein said anionic polymer is the copolymerization product of 2-acrylamido-2-methylpropanesulphonic acid (40 to 70%) and tert-butylacrylamide; a vinyl acetate/ vinyl tert-butyl-benzoate/crotonic acid terpolymer; a copolymer of vinylpyrrolidone and acrylic or methacrylic acid; a copolymer of vinylpyrrolidone, tert-butyl acrylate and acrylic or methacrylic acid; a copolymer of vinylpyrrolidone, lauryl methacrylate and acrylic or methacrylic acid; a methacrylic acid/methyl methacrylate copolymer; or an acrylic acid/N,N-dimethylacrylamide/ethyl methacrylate/ N-tert-butylacrylamide copolymer.

2. A method according to claim 1, wherein the anionic polymer is employed in an amount ranging from 0.1 to 25% by weight.

3. A method according to claim 1, wherein the linear block copolymer is employed in an amount ranging from 0.05 to 20% by weight.

4. A method according to claim 1, wherein the anionic polymer is employed in an amount ranging from 0.5 to 20%.

5. A method according to claim 1, wherein the linear block copolymer is employed in an amount ranging from 0.1 to 10% by weight.

6. A cosmetic composition for maintaining hairstyle comprising in a cosmetically acceptable carrier, a polysiloxane/ polyoxyalkylene linear block copolymer and an anionic polymer, where said polysiloxane/polyoxyalkylene linear block copolymer corresponds to the formula:

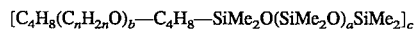

in which:

Me represents methyl;

n is an integer from 2 to 4;

a and b are integers greater than or equal to 4; and c is a number greater than or equal to 4; wherein the average molecular weight of each siloxane block ranges from approximately 400 to approximately 10,000; wherein the average molecular weight of each polyoxyalkylene block ranges from approximately 300 to approximately 10,000; wherein the siloxane blocks represent from approximately 10% to approximately 90% by weight of the block copolymer; and further wherein the average molecular weight of the block copolymer ranges from at least 3,000 to 95,000;

and further wherein said anionic polymer is the copolymerization product of 2-acrylamido-2-methylpropanesulphonic acid (40 to 70%) and tert-butylacrylamide; a vinyl acetate/ vinyl tert-butyl-benzoate/crotonic acid terpolymer; a copolymer of vinylpyrrolidone and acrylic or methacrylic acid; a copolymer of vinylpyrrolidone, tert-butyl acrylate and acrylic or methacrylic acid; a copolymer of vinylpyrrolidone, lauryl methacrylate and acrylic or methacrylic acid; a methacrylic acid/methyl methacrylate copolymer; or an acrylic acid/N,N-dimethylacrylamide/ethyl methacrylate/ N-tert-butylacrylamide copolymer.

7. A cosmetic composition according to claim 6, wherein the anionic polymer is employed in an amount ranging from 0.1 to 25% by weight.

8. A cosmetic composition according to claim 7, wherein the anionic polymer is employed in an amount ranging from 0.5 to 20% by weight.

9. A cosmetic composition according to claim 6, wherein the linear block copolymer is employed in an amount ranging from 0.05 to 20% by weight.

10. A cosmetic composition according to claim 9, wherein the linear block copolymer is employed in an amount ranging from 0.1 to 10%.

* * * * *